United States Patent [19]
Fujiwara et al.

[11] Patent Number: 4,916,069
[45] Date of Patent: Apr. 10, 1990

[54] ENZYME AND PROCESS FOR PRODUCING THE SAME

[75] Inventors: Akiko Fujiwara; Tatsuo Hoshino, both of Kamakura; Teruhide Sugisawa, Yokohama, all of Japan

[73] Assignee: Hoffmann-La Roche Inc., Nutley, N.J.

[21] Appl. No.: 55,271

[22] Filed: May 29, 1987

[30] Foreign Application Priority Data

Jun. 3, 1986 [GB] United Kingdom ................. 8613430
Apr. 14, 1987 [GB] United Kingdom ................. 8708907

[51] Int. Cl.$^4$ .......................... C12N 9/04; C12R 1/01
[52] U.S. Cl. ................................... 435/147; 435/190; 435/252.1; 435/822
[58] Field of Search .................... 435/190, 252.1, 822, 435/147

[56] References Cited

U.S. PATENT DOCUMENTS 3,912,592  10/1975  Makover et al. ................... 435/822

FOREIGN PATENT DOCUMENTS 278447  8/1988  European Pat. Off. ............ 435/138

OTHER PUBLICATIONS

Acta Microbiologica Sinica, 21(2), 185–191 (1981), (Yan et al.).
Krieg, Ed., *Bergey's Manual of Systematic Bacteriology*, vol. 1, pp. 275–278, 1984.
Sato et al., "Enzymic Studies on the Oxidation of Sugars and Sugar Alcohols, VIII . . . ", J. Biochem (Tokyo) 1969, 66(4), 521–7, (CA72:39128j).
Martin et al., "Conversion of L-Sorbose to L-Sorbo-sone . . . ", Biotechnol. Bioeng. 1976, 18(2), 217–37, (CA 84:134083x).
Kitamura et al., Biotechnology and Bioengineering vol. XVII, pp. 349–359, (1975).
Makover et al., Biotechnology and Bioengineering vol. XVII, pp. 1485–1814 (1975).

*Primary Examiner*—Robert A. Wax
*Attorney, Agent, or Firm*—George M. Gould; Bernard S. Leon; William H. Epstein

[57] ABSTRACT

The present invention relates to novel coenyme independent L-sorbose dehydrogenase and a process for producing the same. The enzyme provided by the present invention catalyzes the oxidation of L-sorbose to L-sorbosone, the precursor of 2-keto-L-gulonic acid which is an important intermediate in the production of vitamin C.

Due to the release duties in foreign countries, the original deposits with respect to the following strains have been transferred to the deposit under the Budapest Treaty at Agency of Industrial Science and Technology, Fermentation Research Institute, Japan on Jan. 29, 1987. And the following accession numbers have been allotted to each strain.

| strain | Old No. | New No. |
|---|---|---|
| *Gluconobacter oxydans* UV-10 | FERM-P No. 8422, | Accession No. FERM BP-1267 |
| *Gluconobacter oxydans* E-1 | FERM-P No. 8353, | Accession No. FERM BP-1265 |
| *Gluconobacter oxydans* H-2 | FERM-P No. 8354, | Accession No. FERM BP-1266 |
| *Gluconobacter oxydans* L-8 3441P | FERM-P No. 8355, | Accession No. FERM BP-1268 |

8 Claims, 1 Drawing Sheet

ENZYME AND PROCESS FOR PRODUCING THE SAME

BACKGROUND OF INVENTION

The novel coenzyme independent L-sorbose dehydrogenase is an enzyme which catalyzes the oxidation of L-sorbose to L-sorbosone, the precursor of 2-keto-L-gulonic acid which is an important intermediate for the production of vitamin C.

A reaction to convert L-sorbose to L-sorbosone has been known in microorganisms. L-sorbosone production from L-sorbose using cell free extracts of microorganisms was reported in several prior publications. In U.S. Pat. No. 3,912,592, the microorganisms belonging to the genus Gluconobacter, Pseudomonas, Acinetobacter, Bacillus, Sarcina, Streptomyces, Serratia, Aerobacter, Mycobacterium and Paecilomyces were reported to be capable of such a conversion. Although Makover et al. (Biotechnol. Bioeng. 17, 1485–1514, 1975) described the primary characterization of the enzyme of *Pseudomonas putida* ATCC 21812, they have failed to isolate it. Kitamura et al. (Biotechnol. Bioeng. 17, 349–359, 1975) reported that the activity of L-sorbose dehydrogenase found in Gluconobacter melanogenus IFO 3293 was stimulated by phenazine methosulfate, methylene blue or potassium ferricyanide as an electron acceptor. But they did not isolate the enzyme.

As described above, no purified enzyme has been obtained or prepared which has the activity of catalizing the oxidation of L-sorbose to L-sorbosone.

SUMMARY OF THE INVENTION

It has been found that the purified enzyme isolated from a membrane fraction of cells of specific microorganisms specifically catalyzes the oxidation of L-sorbose to L-sorbosone. The present invention has been accomplished on the basis of this finding.

It is an object of the present invention to provide the novel enzyme having coenzyme independent L-sorbose dehydrogenase activity to convert L-sorbose to L-sorbosone and having high substrate specificity. It is another object to provide a process for producing this novel L-sorbose dehydrogenase enzyme by cultivation of a microorganism belonging to the genus Gluconobacter or a mutant thereof which are capable of producing the novel L-sorbose dehydrogenase in the cells, and isolating said enzyme in pure form from said cells. This isolation can be accomplished by disruption of the cells, and isolation and purification of the enzyme from cell free extract of disrupted cells, preferably from the membrane fraction of microorganisms.

STATEMENT OF DRAWINGS

FIG. 1 is a chromatography of membrane-bound L-sorbose dehydrogenase on a DEAE-Sepharose (Pharmacia Fine Chemical CL-6-B) column.

DETAILED DESCRIPTION

Figure 1:
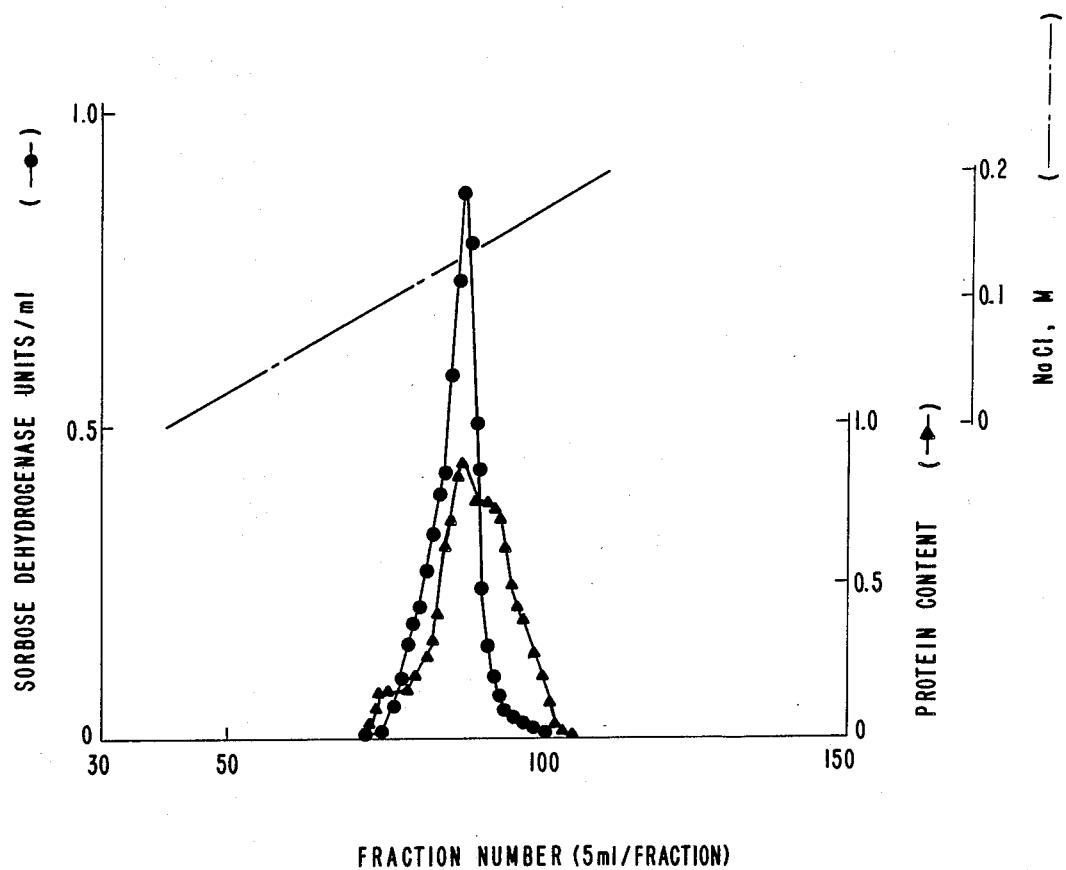

The physico-chemical properties of the purified sample of the novel L-sorbose dehydrogenase prepared by Examples set forth later on are as follows:

(1) Enzyme Activity

L-Sorbose dehydrogenase, i.e. the enzyme of the present invention catalyzes the oxidation of L-sorbose to L-sorbosone in the present of an electron acceptor according to the following reaction formula.

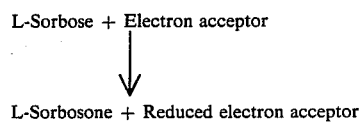

The enzyme does not utilize oxygen as an acceptor. However any conventional compound which has the ability to act as an electron acceptor can be utilized in conjunction with the enzyme of this invention to oxidize L-sorbose to L-sorbosone. As an electron acceptor, 2,6-dichloroindophenol (hereinafter referred to as DCIP), phenazine methosulphate, Wurster's blue, ferricyanide, coenzyme Q or cytochrome C can be used.

Enzyme assay was performed at 25° C. by measuring the decrease of absorbance at 600 nm of DCIP spectrophotometrically. One unit of enzyme activity was defined as the amount of enzyme which catalyzed the reduction of 1 μmole of DCIP per minute. The extinction coefficient of DCIP at pH 7.0 was taken as 14.5 $mM^{-1}$. The basal reaction mixture is shown below. The mixture was prepared just before the assay.

| Basal mixture: | |
|---|---|
| 0.1 M Potassium Phosphate buffer (pH 7.0) containing 0.3% Triton X-100 | 3 ml |
| 2.5 mM DCIP | 0.45 ml |
| $H_2O$ | 4.95 ml |

A cuvette with 1 cm light path contained 0.4 ml of basal mixture, 0.1 ml of 1M L-sorbose, enzyme solution, and water in a final volume of 0.51 ml. A reference cuvette contains all components except the substrate. The reaction was initiated by the addition of the substrate. Enzyme activity was measured as the initial reduction rate of DCIP.

(2) Substrate Specificity

Substrate specificity of the enzyme was determined using the same enzyme assay method as described in the above (1) except that 0.1 ml of each of the various substrate solutions (1M) was used instead of L-sorbose. The results of the measurement are shown in Table 1. It was revealed that the enzyme of the present invention was highly specific for L-sorbose.

Table 1

| Substrate | Relative enzyme activity (%) |
|---|---|
| Sorbose | 100 |
| Glucose | 0 |
| Mannitol | 0 |
| Sorbitol | 0 |
| Fructose | 0 |
| Glycerol | 0 |
| Adonitol | 0 |
| Erythrytol | 0 |
| Na-Gluconate | 0 |
| Ca-Idonate | 0 |
| Mannose | 0 |
| Maltose | 0 |
| Xylose | 0 |
| EtOH | 0 |
| Lactose | 0 |
| Sucrose | 0 |
| Galactose | 0 |
| Cellobiose | 0 |
| Inositol | 0 |

Table 1-continued

| Substrate | Relative enzyme activity (%) |
| --- | --- |
| Arabinose | 0 |

(3) Optimum pH

The correlation between the reaction rate of the L-sorbose dehydrogenase and pH was determined McIlvaine buffer (mixture of 0.1M citric acid and 0.2M disodium phosphate) of various pH's. The result is shown in Table 2.

Table 2

| pH | Relative activity (%) |
| --- | --- |
| 4.0 | 0 |
| 4.5 | 0 |
| 5.1 | 9.4 |
| 5.6 | 35.3 |
| 6.1 | 68.8 |
| 6.6 | 90.0 |
| 7.2 | 100 |
| 7.7 | 95.0 |
| 8.1 | 85.3 |

The enzyme showed the highest enzymatic activity at pH range between 6.5 and 8.0.

(4) pH Stability

The purified enzyme was added to McIlvaine buffer (mixture of 0.1M citric acid and 0.2M disodium phosphate) of various pH's and the mixtures were kept standing for 121 hours at 4° C. The residual activity was assayed under the standard assay condition as described under (1) above. The results of the measurement are shown in Table 3.

Table 3

| pH | Relative activity (%) |
| --- | --- |
| 4.0 | 0 |
| 4.5 | 0 |
| 5.0 | 0 |
| 5.5 | 0 |
| 6.0 | 23.8 |
| 6.5 | 60.0 |
| 7.0 | 100 |
| 7.5 | 75.9 |
| 8.0 | 57.5 |

The purified enzyme was relatively stable at pH's between 6.5 and 8.0.

(5) Heat Stability

The purified enzyme was treated for 5 minutes at various temperatures in 10 mM potassium phosphate buffer (pH 7.0), and then cooled immediately in ice water. The residual activity was measured under the standard assay conditions as described under (1) above. the results are shown in Table 4.

Table 4

| Temperature (°C.) | Relative activity (%) |
| --- | --- |
| 0 | 100 |
| 22 | 100 |
| 25 | 100 |
| 30 | 97.9 |
| 36 | 86.6 |
| 41 | 69.2 |
| 46 | 47.5 |
| 55 | 14.7 |
| 65 | 10.3 |

The purified enzyme was stable up to 30° C., and lost about 50% and 90% of its activity after incubation at 46° C. and 65° C., respectively.

(6) Temperature Dependence of the Activity

The enzymatic activities of L-sorbose dehydrogenase were measured at temperatures from 20° C. to 58° C. in the reaction system as described under (1) above. The results are shown in Table 5.

Table 5

| Temperature (°C.) | Relative activity (%) |
| --- | --- |
| 20 | 28.2 |
| 25 | 26.7 |
| 29 | 35.9 |
| 36 | 50.8 |
| 40 | 70.7 |
| 45 | 93.8 |
| 48 | 100 |
| 55 | 91.8 |
| 58 | 77.0 |

The activity of the enzyme of the present invention increases in accordance with the increase of temperature up to 48° C.

(7) Molecular Weight

The enzyme solution was applied on Sephadex G-200 (1.0×100 cm) columnequilibrated with the 10 mM potassium phosphate buffer (pH 7.0) containing 0.3% Triton X-100 and 0.2M L-sorbose, and developed with the same buffer.

The molecular weight of the enzyme was calculated to be 210,000±20,000 by gel filtration. However, as the enzyme of the present invention is a membrane protein and is solubilized from the membrane using a detergent, the molecular weight obtained may not be the true molecular weight of the enzyme. Polyacrylamide gel electrophoresis of the enzyme in the presence of SDS (sodium dodecyl sulfate) showed a single band at the molecular weight of about 58,000±5,000, demonstrating that the enzyme of the present invention consists of homologous subunits.

(8) Measurements of the Km Value

In the procedure described under (2) above, the velocities of oxidising reactions with varying concentrations of L-sorbose from 0.5 mM to 320 mM were measured to determine the Km value for L-sorbose. The maximum reaction velocity was found at the substrate concentration of about 200 mM. Apparent Michaelis constant (Km) was calculated to be 102±10 mM with DCIP as an electron acceptor.

(9) Effect of Metal Ions

Using the assay procedure described under (1) above, the effect of various metal ions on the enzyme activity was examined. The results of the measurement are shown in Table 6. $Co^{2+}$ and $Fe^{3+}$ were stimulative and $Cu^{2+}$ was inhibitory.

Table 6

| Metal | Concentration (mM) | Relative activity (%) |
| --- | --- | --- |
| $CaCl_2$ | 0.4 | 100 |
|  | 0.8 | 100 |
| $CoC_1 \cdot 6H_2O$ | 0.4 | 109.2 |
|  | 0.8 | 118.4 |
| $CuSO_4$ | 0.8 | 0 |
| $CuSO_4 \cdot 5H_2O$ | 0.08 | 30.9 |

Table 6-continued

| Metal | Concentration (mM) | Relative activity (%) |
|---|---|---|
| $CuCl_2 \cdot 2H_2O$ | 0.4 | 0 |
| $Cu(NO_3)_2 \cdot H_2O$ | 0.3 | 2.27 |
| $Fe(SO_4)_3 \cdot xH_2O$ | 0.4 | 121.3 |
|  | 0.9 | 106.4 |
| $MgSO_4 \cdot 7H_2O$ | 0.4 | 100 |
|  | 0.8 | 100 |
| $MgCl_2 \cdot 6H_2O$ | 0.8 | 83.3 |
| $MnCl_2 \cdot 4H_2O$ | 0.4 | 100 |
|  | 0.9 | 98.3 |
| $MnSO_4 \cdot H_2O$ | 0.4 | 100 |
| $Na_2MoO_4 \cdot 2H_2O$ | 0.3 | 86.1 |
|  | 1.06 | 69.6 |
| TiCl | 0.4 | 100 |
|  | 0.8 | 100 |
|  | 1.8 | 100 |
| $ZnSO_4 \cdot 7H_2O$ | 0.4 | 100 |
|  | 0.9 | 100 |
| $NiSO_4 \cdot 6H_2O$ | 0.4 | 100 |
|  | 0.9 | 100 |
| none | — | 100 |

(10) Effect of Inhibitors

Using the assay procedure described under (1) above, the effect of various inhibitors on the enzyme activity was examined. The results are shown in Table 7. Quinine, monoisodoacetate, sodium fluoroacetate and sodium fluoride inhibited the enzyme activity partially.

Table 7

| Inhibitor | Concentration (mM) | Inhibition (%) |
|---|---|---|
| EDTA | 0.94 | 0 |
|  | 5.2 | 13.3 |
| Quinine | 1.85 | 0 |
|  | 4.24 | 30.5 |
| N-Ethyl-maleimide | 1.85 | 0 |
|  | 4.24 | 0 |
| Sodium Azide | 1.85 | 0 |
|  | 4.24 | 0 |
| Mono-Iodo acetate | 1.85 | 0 |
|  | 4.24 | 34.6 |
|  | 9.37 | 68.5 |
| PCMB (p-chloro-mercuri-benzoate) | 0.02 | 0 |
|  | 0.04 | 0 |
|  | 0.17 | 0 |
| $Na_2HAs \cdot O_4 \cdot 7H_2O$ | 1.85 | 0 |
|  | 4.24 | 0 |
| Sodium Fluoro acetate | 1.85 | 0 |
|  | 4.24 | 8.6 |
|  | 9.37 | 26.5 |
| Sodium Fluoride | 1.85 | 10.3 |
|  | 4.24 | 10.3 |
|  | 9.37 | 22.1 |
| KCN | 0.88 | 0 |

(11) Purification Method

Purification of L-sorbose dehydrogenase may be effected by known purification methods and by combination of known purification methods respectively, such as ion exchange chromatography, liquid chromatography, gel-filtration, gel-electrophoresis, salting out and dialysis.

The L-sorbose dehydrogenase provided by the present invention can be prepared by cultivating an appropriate microorganism, disrupting the cells and isolating and purifying it from cell free extract of disrupted cells, preferably from the membrane fraction of microorganism.

The microorganisms used for the present invention are microorganisms belonging to genus Gluconobacter or mutants thereof. According to the newest classification, all the strains belonging to Gluconobacter fall into the species *Gluconobacter oxydans*. Morphological and physiological characteristics of the strains belonging to *Gluconobacter oxydans* are described in "Bergey's Manual of Systematic Bacteriology", Vol. I, p. 275–278, 1984 and F. Gossele et al., International J. System. Bacteriol, Vol. 33, p. 65–81, 1983.

Microorganisms belonging to the genus Gluconobacter which are used in the present invention can be isolated from natural sources or are available from the culture collections. The mutants derived thereof may also be used according to the present invention.

The mutants used in the present invention can be obtained by treating a wild type strain with a mutagen such as ultraviolet irradiation, X-ray irradiation, γ-ray irradiation or contact with a nitrous acid or other suitable mutagens, or by isolating a clone occurring by spontaneous mutation. These mutations of a wild type strain or a mutant strain thereof may be effected in any of the ways per se well known for the purpose by one skilled in the art. Many of these methods have been described in various publications, for example, "Chemical Mutagens" edited by Y. Tajima, T. Yoshida and T. Kada, published by Kodansha Scientific Inc., Tokyo, Japan, in 1973.

The mutants according to the present invention can also be obtained by fusion of the strains belonging to the species *Gluconobacter oxydans* and the combination of the mutagenesis and/or fusion.

Examples of the strains most preferably used in the present invention are *Gluconobacter oxydans* UV-10, *Gluconobacter oxydans* E-1, *Gluconobacter oxydans* H-2, *Gluconobacter oxydans* L-8 and the like. These microorganisms have been deposited in Agency of Industrial Science and Technology, Fermentation Research institute, Japan under the following deposited No., respectively.

| | |
|---|---|
| Gluconobacter oxydans UV-10 | FERM BP-1267 |
| Gluconobacter oxydans E-1 | FERM BP-1265 |
| Gluconobacter oxydans H-2 | FERM BP-1266 |
| Gluconobacter oxydans L-8 | FERM BP-1268 |

The microorganism may be cultured in an aqueous medium supplemented with appropriate nutrients under aerobic condition. The cultivation may be conducted at pH of 4.0 to about 8.0, preferably from 4.5 to 6.5. A cultivation period varies depending upon the microorganisms and nutrient medium to be used, preferably about 10 to 100 hours. A preferred temperature range for carrying out for the cultivation is from about 10° C. to 40° C., preferably from 25° C. to 35° C.

It is usually required that the culture medium contains nutrients as; assimilable carbon sources such as glycerol, D-mannitol, D-sorbitol, erythritol, ribitol, xylitol, arabitol, inositol, dulcitol, D-ribose, D-fructose, D-fucose, D-glucose, gluconate, L-sorbose, maltose and sucrose, preferably L-sorbose, D-sorbitol or glycerol; digestible nitrogen sources such as organic substances, for example, peptone, yeast extract, soybean meal and corn steep liquor and inorganic substances, for example, ammonium sulfate, ammonium chloride and potassium nitrite; vitamins and trace elements.

In the following, an embodiment for isolation and purification of L-sorbose dehydrogenase from the microorganisms after the cultivation is briefly described.

(1) Cells are harvested from the fermentation broth by centrifugation.

(2) The harvested cells are washed with water, physiological saline or a buffer solution having an appropriate pH.

(3) The washed cells are suspended in the buffer solution and disrupted by means of a homogenizer, sonicator or treatment with lysozyme and the like to give a disrupted solution of cells.

(4) L-sorbose dehydrogenase is isolated and purified from cell free extract of disrupted cells, preferably from the membrane fraction of microorganisms.

The L-sorbose dehydrogenase provided by the present invention is useful as a catalyst for the production of L-sorbosone from L-sorbose. The reaction should be conducted at pH values of from about 5.0 to about 10.0 in the presence of an electron acceptor, for example, DCIP, phenazine methosulfate, Wurster's blue, ferricyanide, coenzyme Q, cytochrome C and the like in a solvent such as phosphate buffer, tris-HCl buffer and the like. A preferred temperature range for carrying out the reaction is from about 20° C. to about 60° C. When the pH and temperature are set at about 6.5-8.0 and 50° C., respectively, reaction usually brings about most preferable results. Concentration of L-sorbose in a solvent varies depending on other reaction conditions but, in general, is desirable to be about 10-100 g/L, most preferably from about 30-40 g/L.

In the reaction, the enzyme may also be used in an immobilized state with an appropriate carrier. Any means of immobilizing enzyme generally known to the art may be used. For instance, the enzyme may be bound directly to a membrane, granules or the like of a resin having functional group(s), or it may be bound through bridging compounds having bifunctional group(s), for example, glutaraldehyde, to the resin.

The following Examples illustrate the present invention.

EXAMPLE 1

Preparation of L-sorbose dehydrogenase (1) Cultivation of *Gluconobacter oxydans* UV-10 (FERM BP-1267)

The agar slant culture of *Gluconobacter oxydans* UV-10(FERM BP-1267) was inoculated into 5 ml of the medium No. 3B in a test tube and cultivated at 27° C. for 3 days on a tube shaker. The medium contained L-sorbose 7.0%, glycerol 0.05%, yeast extract (Oriental Co.) 1.5%, MgSO$_4$.7H$_2$O 0.25 and CaCO$_3$ 1.0%. One ml of this culture was transferred to 50 ml of the same medium in a 500 ml-Erlenmeyer flask, and cultivated at 27° C. for 3 days on a rotary shaker (180 r.p.m.). 800 ml of the culture thus prepared was used as an inoculum for a 30 L jar fermentor containing 20 L of the medium No. 3B. Jar fermentor was operated at 30° C., 400 r.p.m. for agitation and 1 v.v.m. (v.v.m.=volume of air/volume of medium/minute) for aeration. After 40 hours fermentation, the culture was harvested to collect the cells. The broth was centrifuged r.p.m. (365×g) at 1,500/ for 10 minutes to remove calcium carbonate, then at 8,000 r.p.m. (10 000×g) to pellet the cells. The cell cake was washed with 0.85% NaCl once. From 20 L of broth, 374 g (wet weight) of the cells was obtained.

(2) Preparation of Membrane Fraction

The cells of *Gluconobacter oxydans* (77.5 g) from the above step (1) were washed twice with physiological saline. The washed cells were suspended in 230 ml of the buffer and disrupted by a Dyno Mill (Willy, A. Bachofen Co., Basle) homogenizer in the presence of glass beads (0.1 mm o) at 2,000 r.p.m. for 4 minutes. Cell debris was removed by centrifugation at 4000 r.p.m. (1,800×g) for 10 minutes, and then the cell free extract was centrifuged at 40 000 r.p.m. (80,000×g) for 1 hour. The resulting precipitate was collected as the membrane fraction (42 g).

The membrane fraction was suspended in 600 ml of the buffer containing 0.5% Tween 80 and 0.2M L-sorbose. The suspension was stirred for 3 hours and then centrifuged at 40 000 r.p.m. (80,000×g) for 1 hour. Successively, the residual membrane was suspended in 600 ml of the buffer containing 0.3% Triton X-100 and 0.2M L-sorbose. The suspension was stirred for 3 hours and then centrifuged at 40 ooo rp.m. (80,000×g) for 1 hour. The supernatant thus obtained contained the solubilized L-sorbose dehydrogenase. The supernatant was dialyzed overnight against two batches of 2 L of the buffer containing 0.3% Triton X-100 and 0.2M L-sorbose.

(3) Diethylaminoethyl (hereinafter referred to as DEAE)-cellulose column chromatography The dialyzate (570 ml) from the above step was applied to a DEAE-cellulose column (2.5×50 cm) equilibrated with the buffer containing 0.3% Triton X-100 and 0.2M L-sorbose. The column was washed with the same buffer and the enzyme eluted with a linear gradient of NaCl to 0.5M.

(4) DEAE-Sepharose column chromatography

The pooled enzyme fraction (100 ml) from the previous step was dialyzed against two batches of 1 L of the buffer containing 0.3% Triton X-100 and 0.2M L-sorbose, and applied on a DEAE-Sepharose column (1.5×30 cm) equilibrated with the same buffer. After the column was washed with the same buffer, L-sorbose dehydrogenase was eluted with the linear gradient of NaCl to 0.2M as shown in FIG. 1. Fractions from 87 to 89 were pooled (15 ml), and used for next purification step.

(5) Sephadex G-200 column chromatography

A portion of the enzyme fraction (2 ml) was applied on Sephadex G-200 column (1.0×100 cm) equilibrated with the same buffer and developed. The active fraction was pooled and stored at −80° C. Summary of the purification steps of the enzyme is shown in Table 8.

TABLE 8

| Step | Total protein (mg) | Total activity (units) | Specific activity (units/mg) | Yield (%) |
| --- | --- | --- | --- | --- |
| Cell-free extract | 7152 | 125.9 | 0.0176 | 100 |
| Membrane fraction | 2565 | 115.1 | 0.0449 | 91.4 |
| Solubilized membrane fraction | 504.5 | 78.04 | 0.155 | 62.0 |
| DEAE-cellulose | 120.0 | 59.75 | 0.498 | 47.5 |
| DEAE-Sepharose | 38.35 | 29.44 | 0.768 | 23.4 |
| Sephadex G-200* | 0.6 | 0.538 | 0.897 | |

*Only a portion of the fraction from DEAE - Sepharose column chromatography was used for this step.

(6) Purity of the isolated enzyme

For estimation of purity of the enzyme isolated, a polyacrylamide gel electrophoresis (separating gel; 5% acrylamide, conditions of electrophoresis: 20 mA at 4°

C. for 8 hours) was performed. The enzyme yielded a single band, and it was confirmed that this protein had enzyme activity by staining with the solution of 0.05M phosphate buffer (pH 7.0) containing 50 mM L-sorbose; 40 µg/ml of nitroblue tetrazolium and 140 µg/ml of phenazine methosulfate for 30 minutes.

Sodium dodecyl sulfate (SDS) polyacrylamide gel electrophoresis (separating gel; 15% acrylamide, conditions of electrophoresis; 20 mA at room temperature for 3 hours) was performed to estimate the purifity and to determine the molecular structure of the enzyme. As a result, the enzyme yielded a single band with a molecular weight of 58,000±5,000. As molecular weight standards, phosphorylase B (MW, 92,500), bovine serum albumin (MW, 66,200), ovalbumin (MW, 45,000), carbonic anhydrase (MW, 31,000), soybean trypsin inhibitor (MW, 21,500) and lysozyme (MW, 14,400) were used.

(7) Identification of the reaction product

The reaction mixture containing 0.2 ml of the purified enzyme, 0.05 ml of 0.5M potassium phosphate buffer (pH 7.0), 0.05 ml of 1M L-sorbose, 0.02 ml of 0.2M phenazine methosulfate, and water in a final volume of 0.5 ml was incubated for 30 minutes at 45° C. The reaction product was analyzed by thin layer chromatography and high pressure liquid chromatography. As a result, the product was identified to be L-sorbosone in comparison with an authentic sample.

EXAMPLE 2

In the same manner as described in Example 1, L-sorbose dehydrogenase was isolated from the strains *Gluconobacter oxydans* E-1 (FERM BP-1265), H-2 (FERM BP-1266) and L-8 (FERM BP-1268) and characterized. As a result, the enzymes from these strains showed identical properties with those of the enzyme from *Gluconobacter oxydans* UV-10 (FERM BP-1267).

EXAMPLE 3

The reaction mixture containing 100 ml of cell free extract of UV-10, FERM BP-1267 (total enzyme activity, 123 units), as prepared by the manner as described in steps (1) to (2) of Example 1, 50 ml of 0.5M potassium phosphate buffer (PH 6.0), 50 ml of 1M L-sorbose solution, 10 ml of 0.2M phenazine methosulfate solution and 290 ml of water was incubated at 30° C. with gentle shaking. As a result, L-sorbosone was formed with the rate of 142 mg/hr.

EXAMPLE 4

The reaction mixture containing 400 ml of purified membrane-bound L-sorbose dehydrogenase (total activity, 120 units), as prepared by the manner as described in steps (1) to (5) of Example 1, 50 ml of 0.5M potassium phosphate buffer (pH 6.0). 50 ml of 1M L-sorbose solution and 10 ml of 0.2M phenazine methosulfate solution was incubated at 30° C. with gentle shaking. As a result, L-sorbosone was formed with the rate of 224 mg/hr.

We claim:

1. The enzyme L-sorbose dehydrogenase as a pure single protein.

2. The enzyme of claim 1 wherein said protein has the ability to catalyze the oxidation of L-sorbose to L-sorbosone.

3. The enzyme of claim 2 wherein said pure protein consist of one unit having molecular weight of 58,000±5,000M as measured by sodium dodecyl sulfate polyacrylamide gel electrophoresis.

4. A process of producing L-sorbosone comprising oxidizing L-sorbose in an inert solvent medium to form L-sorbosone, said oxidation being carried out in said solvent medium containing as a catalyst the enzyme L-sorbose dehydrogenase in the form of a single pure protein.

5. The process of claim 4 wherein said oxidation is carried out at pH of from about 5 to about 10.

6. The process of claim 5 wherein said reaction is carried out at a temperature of about 20° C. to about 60° C.

7. The process of claim 6 wherein the concentration of L-sorbose in said solvent medium is from about 10 to about 100 g/liter.

8. The process of claim 7 wherein said oxidation is carried in the presence of an electron acceptor.

* * * * *